US011992425B2

(12) United States Patent
Pudas et al.

(10) Patent No.: US 11,992,425 B2
(45) Date of Patent: May 28, 2024

(54) SPRING LOADED MEDICAL DEVICE

(71) Applicant: PICOSUN OY, ESPOO (FI)

(72) Inventors: Marko Pudas, Espoo (FI); Niku Oksala, Tampere (FI)

(73) Assignee: PICOSUN OY, Espoo (FI)

( * ) Notice: Subject to any disclaimer, the term of this patent is extended or adjusted under 35 U.S.C. 154(b) by 38 days.

(21) Appl. No.: 16/832,300

(22) Filed: Mar. 27, 2020

(65) Prior Publication Data

US 2020/0352749 A1 Nov. 12, 2020

Related U.S. Application Data

(60) Provisional application No. 62/826,425, filed on Mar. 29, 2019.

(51) Int. Cl.
*A61F 2/82* (2013.01)

(52) U.S. Cl.
CPC ........ *A61F 2/82* (2013.01); *A61F 2210/0004* (2013.01); *A61F 2220/005* (2013.01); *A61F 2240/001* (2013.01); *A61F 2250/0031* (2013.01); *A61F 2250/0067* (2013.01)

(58) Field of Classification Search
CPC ........... A61F 2220/005; A61F 2/06–2002/068; A61F 2/82–2/89; A61F 2/90–2/97
See application file for complete search history.

(56) References Cited

U.S. PATENT DOCUMENTS

| 5,964,744 | A | 10/1999 | Balbierz et al. |
| 2009/0234432 | A1* | 9/2009 | Pacetti ................ B29C 65/4895 |
| | | | 264/282 |
| 2010/0137977 | A1* | 6/2010 | Gregorich ............... A61L 31/08 |
| | | | 623/1.42 |
| 2012/0177910 | A1 | 7/2012 | Weber et al. |
| 2017/0290686 | A1* | 10/2017 | Sirhan ....................... A61F 2/90 |
| 2018/0125684 | A1* | 5/2018 | DeGraaf ................. A61F 2/042 |

FOREIGN PATENT DOCUMENTS

EP 1 604 697 A1 12/2005

OTHER PUBLICATIONS

Extended European Search Report issued in European Patent Application No. 20 165 599.0 dated Aug. 24, 2020.

* cited by examiner

*Primary Examiner* — Keri J Nelson
*Assistant Examiner* — Rebecca Lynee Zimmerman
(74) *Attorney, Agent, or Firm* — NIXON & VANDERHYE

(57) ABSTRACT

A structure is provided comprising a number of surfaces 10, 20 joined together with an adhesive 30, said structure being configured to reshape upon at least partial degradation of the adhesive 30. Related method and uses are further provided.

16 Claims, 3 Drawing Sheets

SPRING LOADED MEDICAL DEVICE

FIELD OF THE INVENTION

The present invention generally relates to manufacturing of implantable medical devices. In particular, the invention pertains to a spring-loaded medical device, a method of its manufacturing and related uses.

BACKGROUND

Stents are medical devices used to maintain patency, viz. the condition of being open or unobstructed, of different stenosed tubes in the human body. The areas of applications range from the cardiovascular system characterized by a high cyclical luminal pressure to that in the urinary, gastrointestinal and respiratory tracts characterized by a pressure at a lower magnitude and changing much less.

In the treatment of arterial stenoses or occlusions (abnormal narrowing or blockage, accordingly, of a blood vessel or any other tubular and/or hollow organ or a structure, the stents are used post-angioplasty, for example, e.g. after the percutaneous transluminal angioplasty (PTA). PTA is an initial treatment option in patients in need of widening the narrowed or obstructed arteries or veins, typically in treatment of atherosclerosis. Utilization of stents is essential, due to the fact, that the long-term (2 years and more) patency rate with PTA alone (without the stent placement) tends to vary between about 40% to about 70%. After the PTA procedure, stents counteract on immediate elastic recoil of the arterial wall and fix plaque(s) against the arterial wall, thus establishing an optimal flow through the treated area.

Common drawbacks encountered with some stents, especially drug eluting stents with thin stent struts and otherwise susceptible stent designs, relate to a fact that these stents may be a subject to recoil (stent recoil).

Stent recoil after the PTA procedure is problematic since it requires re-intervention if the flow through a channel/a cavity is significantly reduced. With respect to any one of such conditions as: airway stenoses and occlusions caused by inflammatory processes or by any other processes affecting structural integrity of the airways; tumors compressing the airways externally or stenosing the airway internally, e.g. endobronchially or endotracheally; loss of cartilage support arising from tumor destruction or formation of malignant tracheoesophageal fistula, the stent is used to dilate the stenosis open and to retain the situation for a maximal time period.

The same principles apply to the tumors in the gastrointestinal tract and in the urinary system. Due to pressure conditions, created especially during the stenoses of the airways and, to some extent, of the gastrointestinal tract and the urinary system, the stents placed in the above mentioned locations are more susceptible to recoil than those placed within the circulatory system.

There is, therefore, a considerable need to modulate the radial force exerted by medical devices, such as stents, within the body channels and/or cavities, i.e. the force generated by the stent outwards against the surrounding tissue. Means to increase the radial force remotely, after the initial operation (e.g. the PTA procedure) would enable re-establishment of the patency postoperatively in case of late stent recoil.

SUMMARY OF THE INVENTION

An objective of the present invention is to solve or to at least alleviate each of the problems arising from the limitations and disadvantages of the related art. The objective is achieved by various embodiments of a structure, a method for manufacturing the structure, and related uses.

In an aspect, a structure is provided according to what is defined in the independent claim 1.

In embodiment, the structure comprises a number of surfaces joined together with an adhesive, and the structure is further configured to reshape upon at least partial degradation of the adhesive.

In embodiments, the adhesive is a biocompatible and/or biodegradable adhesive.

In embodiments, the adhesive is a biocompatible and/or biodegradable polymer.

In embodiment, the adhesive is established on the surfaces of the structure by at least one layer provided as an Atomic Layer Deposition (ALD) layer.

In embodiment, the structure is configured as a medical device. In embodiment, the structure is configured as an implantable medical device. In embodiment, the structure is configured as a stent, such as an implantable stent.

In embodiment, the structure is configured to bear mechanical load, such as spring load, which is released upon at least partial degradation of the adhesive. In embodiment, the structure is configured for a gradual release of spring load by modulating degradation rate of the adhesive.

In embodiment, the structure is configured as a receptacle for at least one chemical substance. In embodiment, the structure is configured to release said at least one chemical substance upon being reshaped due to at least partial degradation of the adhesive. In embodiment, the chemical substance comprises at least one pharmaceutically active agent.

In an aspect, a method for manufacturing the structure is provided, according to what is defined in the independent claim 13.

In another aspect, a method for delivering a pharmaceutically active agent into the body is provided, according to what is defined in the independent claim 14.

In still further aspect, use of an ALD-deposited coating as an adhesive in a medical device is provided, according to what is defined in the independent claim 16.

Without limiting the scope and interpretation of the patent claims, certain technical effects of one or more of the example embodiments disclosed herein are listed in the following.

Thin film deposition, such as atomic layer deposition (ALD) is able to fill small cavities with very high aspect ratios. Essentially all solid surfaces having gaps and/or pores can be conformally coated. When the sidewalls of the said gap are kept stationary during the deposition, the deposition material works as a glue.

Various materials deposited with ALD can degrade or (bio)decompose due to long-term exposure to biological fluids. Alternatively, mechanical force, induced by embedding surroundings, such as channels and/or cavities in human body (e.g. when the human has an implant placed into said channel/cavity), or by a physician with various known means, such as by applying specific physical force.

In some instances related to uses of implanted material, release of applied force, such as stitches, can occur after healing.

The invention allows for producing a medical device structure, such as a stent structure, for example, that expands over a predetermined period of time, while resisting a compressive force. This is important, when the stent is intended to be placed into the locations, within the patient's body, normally experiencing compression from the outside and rendered prone to narrowing/obstructions, accordingly. Likewise, if e.g. a blood vessel's internal cavity begins to narrow over time, the expansion provided by the medical device according to the present disclosure, will effectively resist that.

In the present disclosure, materials with a layer thickness below 1 micrometer (μm) are referred to as "thin films".

The expression "a number of" refers herein to any positive integer starting from one (1), e.g. to one, two, or three; whereas the expression "a plurality of" refers herein to any positive integer starting from two (2), e.g. to two, three, or four.

The term "element" may herein refer also to a multi-part element with multiple functionally and optionally also physically connected elements in addition to single-part or integrated elements.

The terms "first" and "second" are not intended to denote any order, quantity, or importance, but rather are used to merely distinguish one element from another.

BRIEF DESCRIPTION OF THE DRAWINGS

The invention will now be described, by way of example only, with reference to the accompanying drawings, in which.

DETAILED DESCRIPTION

Figure 1:
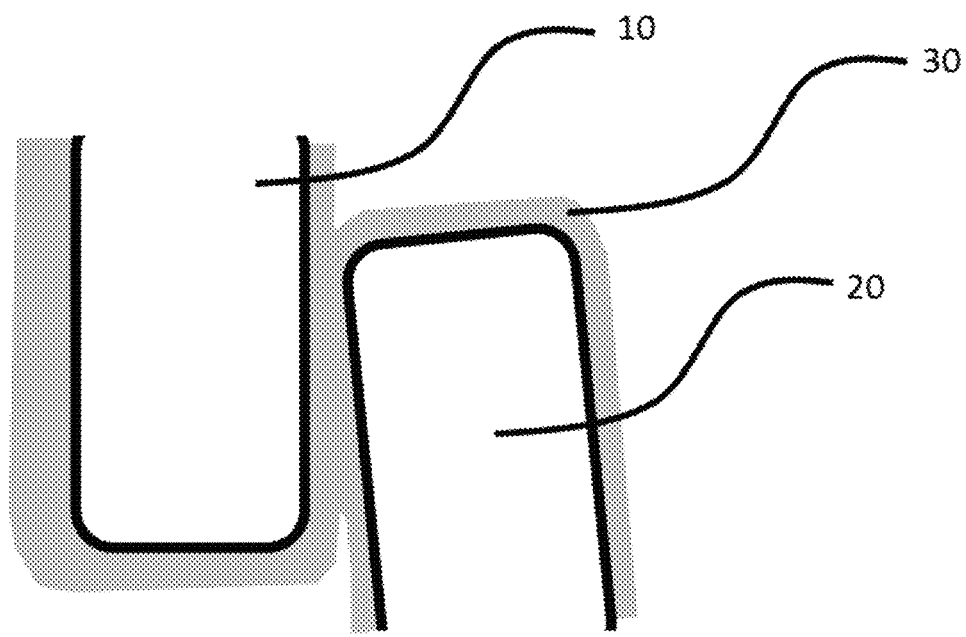
FIG. 1 is a cross-section of two exemplary surfaces held together with an adhesive.

The invention, according to one aspect, pertains to provision of a structure 100 comprising a number of surfaces or elements 10, 20 joined together with an adhesive 30 (FIG. 1). The structure can comprise any number of the surfaces 10, 20. Thus, a relatively simple exemplary structure (a receptacle with a lid) can be provided that employs essentially two surfaces. The structure can be provided as a complex structure comprising hundreds (or more) of the surfaces/the elements, designated as 10, 20 on FIG. 1.

The adhesive 30 is established on the surfaces 10, 20 by at least one coating layer or a coating film. The coating layer can be provided as an Atomic Layer Deposition (ALD) layer. The adhesive 30 is established on all available (within the structure 100) surfaces 10, 20. In some instances, the adhesive layer is established on/between a (pre)selected number of the surfaces 10, 20.

In practice, the adhesive 30 is applied onto all surfaces 10, 20 provided within the structure. ALD coating is a conformal coating and it coats all surfaces equally. However, selectively applied growth inhibitors can be used to enable ALD growth only on selected places (surfaces 10, 20). Self-assembly monolayers, such as that of long-chain alkyl-silanes, hinder or prevent chemically deposited coating films/layers from growing on the substrate and can be used as film growth inhibitors. Additionally or alternatively, photon-enhanced ALD or plasma-assisted ALD can exert pattering effect with a mask, causing the deposition to form only on exposed areas.

The basics of an ALD growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness. In some instances, Chemical Vapour Deposition (CVD) may be utilized.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: MLD (Molecular Layer Deposition), plasma-assisted ALD, for example PEALD (Plasma Enhanced Atomic Layer Deposition) and photon-enhanced Atomic Layer Deposition (known also as photo-ALD or flash enhanced ALD). The process can also be an etching process, one example of which being an ALE process.

ALD is based on alternating self-saturative surface reactions, wherein different reactants (precursors) provided as chemical compounds or elements in a nonreactive (inert) gaseous carrier are sequentially pulsed into a reaction space accommodating a substrate. Deposition of a reactant is followed by purging the substrate by inert gas. Conventional ALD deposition cycle proceeds in two half-reactions (pulse A—purge A; pulse B—purge B), whereby a layer of material is formed in a self-limiting (self-saturating) manner, typically being 0.05-0.2 nm thick. Typical substrate exposure time for each precursor ranges within 0.01-1 seconds.

Pulse A comprises a first precursor in a gaseous phase (first precursor vapor) and pulse B comprises a second precursor in a gaseous phase (second precursor vapor). Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

In the following description, Atomic Layer Deposition (ALD) technology is used as a preferred method.

FIG. 1 thus shows two surfaces (elements) 10, 20 held together during the deposition process, whereby the surfaces are adhered to one another by virtue of a material deposited thereto, viz. the adhesive 30. By means of said adhesive 30, the surfaces 10, 20 are fixedly held together.

The adhesive 30 is formed by at least one coating layer produced during at least one cycle of a chemical deposition process, accordingly. In some instances, the at least one chemical deposition cycle is an ALD deposition cycle.

In some configurations, the adhesive 30 comprises or consists of a biocompatible and/or biodegradable material.

In some additional configurations, the adhesive 30 comprises or consists of a biocompatible and/or biodegradable polymer. The adhesive 30 can be configured for gradual release.

In some configurations, the structure 100 is a medical device, such as an implantable medical device. The structure can be a mesh structure (e.g. mesh wire), optionally a mesh tube. In embodiment, the structure 10 is a stent.

The structure 100 is configured such, as to bear a mechanical (pre)load, such as spring load, which is released upon at least partial degradation of the adhesive 30. At least partial degradation of the adhesive 30 causes the structure 100 to reshape. Reshaping can be viewed as a process of restoring the "original" (intended for use or operative) shape of said structure (from a condition with pre-applied mechanical load).

The present disclosure thus provides for the structure 100 configured as a mechanical assembly, that structure will reshape and/or self-deform itself (for example, spring out) upon at least partial degradation or dissolution of the (biocompatible and/or biodegradable) adhesive material 30 deposited on/between the elements/the surfaces 10, 20.

Reshaping occurs by virtue of release, upon degradation of the adhesive 30, of mechanical (pre)load, such as spring load, applied onto the structure.

Release of spring load can be caused by application of (external) mechanical force onto the structure. Thus, the structure can be configured to reshape/deform upon collapse of a vascular stent, for example, whereby mechanical force is applied onto the structure causing release of the spring load.

Figure 2:
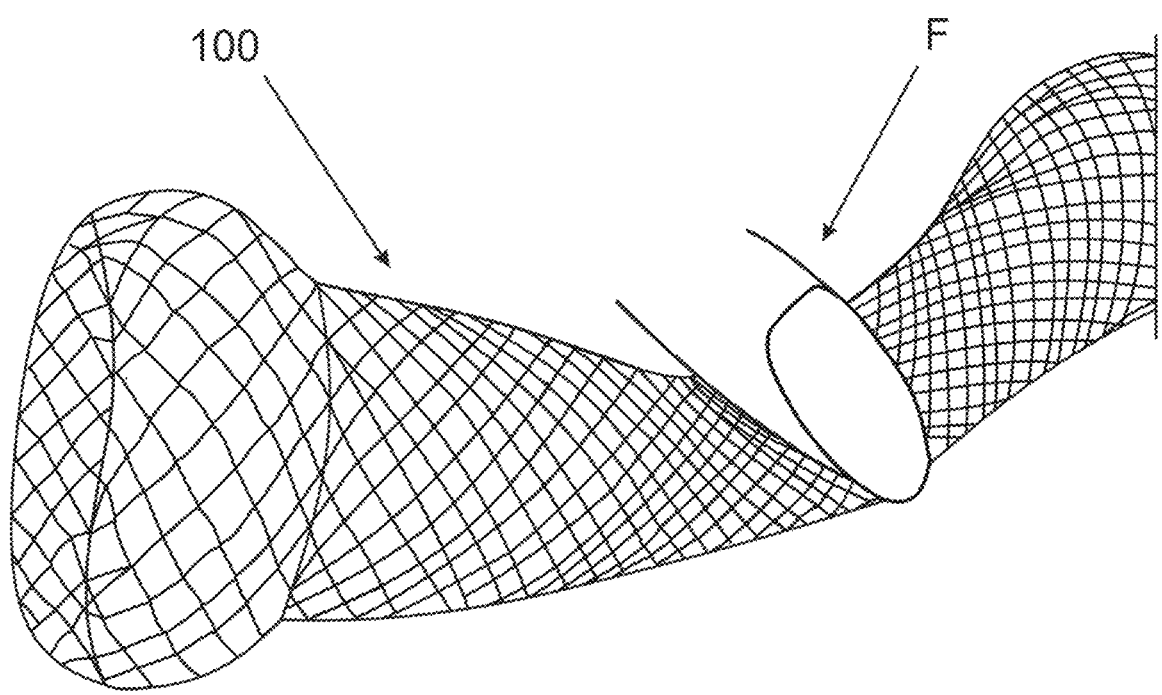
FIG. 2 shows an exemplary configuration of the structure, according to an embodiment, configured as a stent; where said stent is collapsed upon mechanical force.

FIG. 2 illustrates a situation with the exemplary medical structure configured as a stent is collapsed under mechanical force (F). In its open shape, the stent is provided as an essentially tubular structure. In the example illustrated by FIG. 2, the mechanical force (F) is exerted on the structure 100 upon pressing it with a finger.

The same situation (collapse of the stent) can happen with a conventional stent placed in the human body, for example. To fix such situation (reshape the stent), a medical intervention, such as vascular surgery, is often required. By provision of the spring loaded structure 100 according to the present disclosure, release of the spring load, triggered by dissolution of the adhesive 30, causes generation of local stress at the contact points established at those predetermined elements/surfaces 10, 20 previously joined together by said adhesive (and detaching from one another when the adhesive is dissolved). Inducing more stress in the stent structure causes the stent to acquire an essentially tubular (open) shape again.

Figure 3:
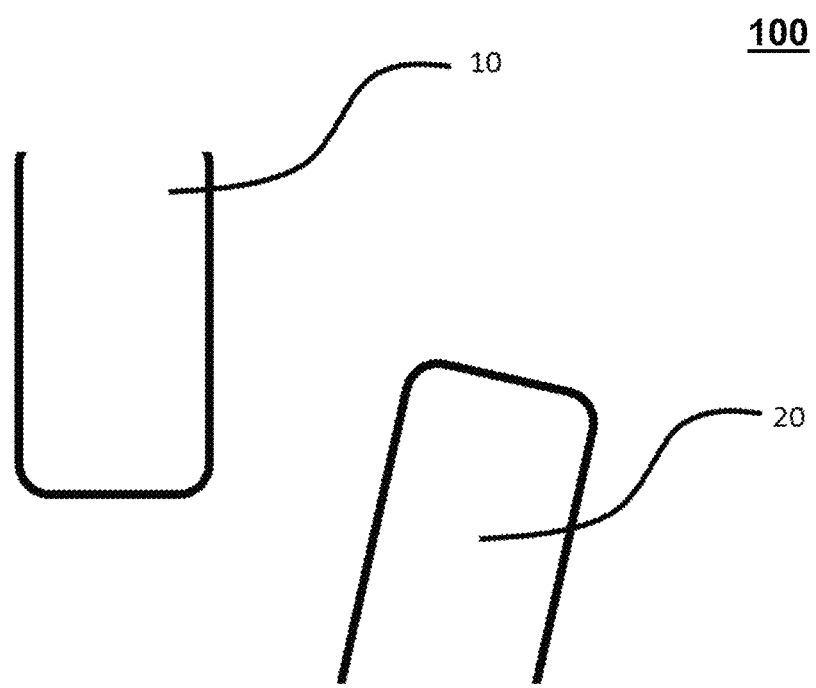
FIG. 3 is a cross-section of two exemplary surfaces separated after the adhesive has degraded.

FIG. 3 shows the structure 100 after reshaping (the release of spring load) and so having the adhesive 30 dissolved. The parts 10 and 20 can move freely.

In practice, the stent 100 with a pre-applied mechanical load (e.g. spring load) created by "gluing" pre-determined elements or surfaces thereof 10, 20 together with the adhesive 30 is inserted into a blood vessel, for example. Upon gradual degradation/release of the adhesive in biological fluid(s), the stent structure 100 reshapes itself into an essentially tubular (open) form, thereby acting as a scaffold onto the blood vessel and keeping the vessel open for unhindered blood flow therethrough.

In additional or alternative configurations, the structure 100 is configured as a receptacle for at least one chemical substance. In such an event the structure may comprise a group of elements that form a receptacle and optionally a group of elements that form a lid or any other appropriate arrangement joined to the receptacle by means of adhesive 30. The elements having surfaces 10, 20 detach from one another upon at least partial degradation and/or dissolution of said adhesive in the body.

The structure 100 consisting of or comprising the receptacle for the at least one chemical substance is preferably configured to release said chemical substance upon being reshaped due to at least partial degradation of the adhesive 30.

The chemical substance comprises at least one pharmaceutically active agent. In some instances, the chemical substance is a pharmaceutical preparation comprising said at least one pharmaceutically active agent. The medical device 100 can thus be configured to carry at least one pharmaceutical preparation therein. The medical device can be configured to carry a number of medicinal preparations (drugs) at once.

The structure 100 according to the present disclosure is thus configured to release said at least one pharmaceutically active agent upon being reshaped and/or self-deformed due to at least partial degradation of the adhesive 30 in the body.

By applying the adhesive onto predetermined elements 10, 20 within the structure 100, the spring load release effect can be adjusted to cause at least partial opening of a predetermined section of the implanted item (viz. the medical device), which action shall release a medicine/a pharmaceutical preparation comprising at least one pharmaceutically active agent.

Various medical applications can benefit from provision of dissolving adhesives in medical devices. These include controlled drug release occurring upon dissolution, optionally gradual dissolution, of the medical device structure 100. In a non-limiting manner, the adhesive 30 can be manufactured from a variety of materials and by different methods in order to be applicable onto different surfaces (e.g. surfaces made of metal, plastics or a combination thereof).

The medical structure 100 configured as a stent (see FIG. 2) can be disposed in a variety the tubular structures in the patients' body, but especially in those tubular structures formed by lumens with low pressure and being exposed to external pressure variations (e.g. respiratory and thoracic internal pressure).

The present disclosure primarily provides for structures configured as medical devices, e.g. stents, for human patients. However, upon modification in appropriate manner, the structure is applicable also to non-human animals, e.g. mammals.

The structure can be further configured for a gradual spring load release as a function of time, for example, whereby recoil-susceptible stents could be expanded "automatically" (i.e. by itself).

In embodiment, the structure is thus configured for a gradual release of spring load by modulating degradation rate of the adhesive 30. Degradation/dissolution rate of said adhesive 30 in in bodily fluids and tissues can be controlled in terms of at least composition and/or thickness or the ALD layer or layers.

By varying deposition chemicals (precursors) and/or a number of deposition layers, the adhesive 30 can be configured to modulate release rate of a drug (constant, accelerated, slowed down) and/or to establish drug release with prominent phases (e.g. initially constant or accelerated or slowed down (phase I); followed by another phase, different from the previous one (Phase II), etc.). Additionally, the adhesive 30 can be applied onto the predetermined locations (elements 10, 20) within the structure to create compartments, for example, to render to structure 100 capable of containment and release different drugs at different time points.

The adhesive 30 can be made with various materials; however, it is critical that upon breaking of/dissolving of said material, no toxic substance is eluted into the body that could possibly block micro vascular pathways and/or have a harmful effect onto the patient. Therefore, it is beneficial that the adhesive layer that is applicable by the ALD techniques is extremely thin (0.1-100 nm).

By way of example, the adhesive 30 can comprise at least one coating layer made of aluminium oxide ($Al_2O_3$), magnesium oxide (MgO), silicon dioxide ($SiO_2$) and/or a combination thereof. It should be noted, that mentioned compounds and/or combinations thereof, in order to be dissolvable in biological fluids, for example, should be manufactured in predetermined reaction conditions and with predetermined precursors to produce a compound of suitable quality.

Further thin layers can be applied to very small structures, such as sub-millimeter sized capsules, items, or walls of such exemplary structures as a stent. Benefit of using ALD is that it enables deposition of thin and pinhole-free layers of adhesives and further provides versatility in choice of said adhesive materials.

For example, an aspect ratio for a sub-micrometer cavity filling has been demonstrated to be higher than 1000:1 (1000:1=depth-to-width aspect ratio), at an exemplary installation Picosun R-200 Advanced ALD system available from Picosun Oy, Finland.

The invention further pertains to a method for manufacturing a structure 100, which method comprises obtaining a structure with the surfaces 10, 20 and joining a plurality of surfaces, optionally, (pre)selected surfaces, together with an adhesive 30. The structure thus obtained is configured to reshape, viz. to restore its original shape by acquiring the shape it had prior the surfaces have been joined together, when the adhesive 30 at least partially degrades (e.g. in bodily fluid). In the method, the adhesive 30 is applied onto the surfaces 10, 20 by Atomic Layer Deposition (ALD). The adhesive can be applied onto all available surfaces 10, 20 within the structure 100 to create a mechanical load effect (such as the spring load effect discussed herein above). In some instances, the adhesive can be applied onto some (pre)selected surfaces.

Still further, the invention pertains to a method for delivering at least one pharmaceutically active agent into the body. In the method, the pharmaceutically active agent is provided in a structure 100 comprising a number of surfaces 10, 20 joined together with an adhesive 30, which structure is configured to release said pharmaceutically active agent upon at least partial degradation of the adhesive 30 in the body. In the method, the structure 100 is preferably configured to release said at least one pharmaceutically active agent upon being reshaped by virtue of at least partial degradation of the adhesive 30 in the body, in particular, in bodily fluids. The method allows for delivery of at least one pharmaceutically active agent into the body of a human patient or, alternatively, a non-human animal, e.g. a non-human mammal.

In an aspect, use of a chemically deposited coating, such as an ALD-deposited coating, as an adhesive in a medical device is further provided. Mentioned use preferably pertains to a medical device configured as an implantable medical device, such as a stent.

It shall be appreciated by those skilled in the art that the embodiments set forth in the present disclosure may be adapted and combined as desired. The disclosure is thus intended to encompass any possible modifications of the device and the deposition method, recognizable by those of ordinary skill in the art, within a scope of appended claims.

The invention claimed is:

1. A structure, comprising:
   a plurality of surfaces; and
   an adhesive layer, as an Atomic Layer Deposition (ALD) coating layer of thickness 0.1-100 nm on all surfaces of the structure,
   wherein the plurality of surfaces are joined together by the adhesive layer in a first configuration having a collapsed shape,
   wherein the structure in the first configuration bears a mechanical load resulting from the adhesive layer joining said plurality of surfaces together and forming the collapsed shape, and
   wherein the adhesive layer is configured to at least partially degrade and thereby permit the plurality of surfaces to detach from one another and release the mechanical load, the structure configured so that when the mechanical load is released the structure reshapes itself from the collapsed shape into a second configuration having an original shape corresponding to a shape the structure had prior to the surfaces being joined together by the adhesive layer.

2. The structure of claim 1, wherein the adhesive layer is biocompatible and/or biodegradable.

3. The structure of claim 1, configured as a medical device.

4. The structure of claim 1, configured as an implantable medical device.

5. The structure of claim 1, configured as a stent.

6. The structure of claim 1, configured for a gradual release of the mechanical load by modulating a degradation rate of the adhesive layer.

7. The structure of claim 1, configured to release at least one chemical substance upon being reshaped due to at least partial degradation of the adhesive layer.

8. The structure of claim 7, wherein the chemical substance comprises at least one pharmaceutically active agent.

9. The structure of claim 1, wherein the adhesive layer comprises at least one ALD-deposited coating layer made of any of aluminium oxide ($Al_2O_3$), magnesium oxide (MgO), and silicon dioxide ($SiO_2$).

10. The structure of claim 1, formed of a mesh wire.

11. The structure of claim 1, wherein the pre-applied mechanical load is a spring load.

12. A method for manufacturing a structure, comprising:
    obtaining a structure having a plurality of surfaces, said structure configured to have an original shape;
    applying an adhesive to all surfaces of the structure by Atomic Layer Deposition (ALD); and
    joining said surfaces together with the adhesive so that said structure assumes a collapsed shape different from said original shape,
    wherein the structure is configured to bear a mechanical load when in the collapsed shape and held by the adhesive, and
    wherein the adhesive is configured to at least partially degrade in order to permit release of the mechanical load and thereby cause the collapsed structure to reshape and acquire the original shape that the structure had prior to the surfaces being joined together.

13. A method for delivering at least one pharmaceutically active agent into the body, wherein said at least one pharmaceutically active agent is provided in a structure comprising a plurality of surfaces joined together with an adhesive provided in the form of a coating layer applied by Atomic Layer Deposition (ALD), wherein said structure is configured to release said pharmaceutically active agent upon at least partial degradation of the adhesive in the body.

14. The method of claim 13, wherein the structure is configured to release said at least one pharmaceutically active agent upon being reshaped by virtue of at least partial degradation of the adhesive in the body.

15. A medical device comprising the structure of claim 1.

16. The medical device of claim 15, wherein the medical device is implantable.

* * * * *